United States Patent [19]

Geoghegan et al.

[11] Patent Number: 4,917,899
[45] Date of Patent: * Apr. 17, 1990

[54] CONTROLLED ABSORPTION DILTIAZEM FORMULATION

[75] Inventors: Edward J. Geoghegan; Seamus Mulligan, both of Athlone, Ireland; Donald E. Panoz, Tuckerstown, Bermuda

[73] Assignee: Elan Corporation plc, Athlone, Ireland

[*] Notice: The portion of the term of this patent subsequent to Jan. 2, 2007 has been disclaimed.

[21] Appl. No.: 121,224

[22] Filed: Nov. 16, 1987

Related U.S. Application Data

[63] Continuation-in-part of Ser. No. 684,661, Dec. 20, 1984, Pat. No. 4,721,619.

[30] Foreign Application Priority Data

Oct. 16, 1987 [IE] Ireland .................................. 2789/87

[51] Int. Cl.$^4$ .......................... A61K 9/12; A61K 9/16; A61K 9/26
[52] U.S. Cl. .................................... 424/461; 424/459; 424/462; 424/470; 424/493; 424/494; 424/495; 424/497
[58] Field of Search ............... 424/489, 474, 477, 479, 424/481, 482, 490, 461, 493, 494, 497, 459, 462, 470

[56] References Cited

U.S. PATENT DOCUMENTS

| | | | |
|---|---|---|---|
| 3,965,255 | 6/1976 | Bloch et al. | 424/472 |
| 4,230,687 | 10/1980 | Sair et al. | 514/965 |
| 4,263,273 | 4/1981 | Appelgren et al. | 424/19 |
| 4,361,546 | 11/1982 | Stricker et al. | 424/462 |
| 4,432,966 | 2/1984 | Zeitoun et al. | 424/471 X |
| 4,496,558 | 1/1985 | DeMarinis et al. | 514/213 |
| 4,499,066 | 2/1985 | Moro et al. | 424/22 |
| 4,555,399 | 11/1985 | Hsiao | 424/80 |
| 4,592,753 | 6/1986 | Panoz | 604/897 |
| 4,606,909 | 8/1986 | Bechgaard et al. | 424/482 X |
| 4,609,542 | 9/1986 | Panoz et al. | 424/19 |
| 4,610,870 | 9/1986 | Jain et al. | 424/19 |
| 4,660,645 | 7/1986 | Ghebre-Sellassie et al. | 424/19 |
| 4,666,702 | 5/1987 | Junginger | 424/497 |
| 4,684,516 | 8/1987 | Bhutani | 424/471 X |
| 4,756,911 | 7/1988 | Drost et al. | 424/472 X |

FOREIGN PATENT DOCUMENTS

| | | | |
|---|---|---|---|
| 0013262 | 7/1980 | European Pat. Off. | |
| 0077956 | 5/1983 | European Pat. Off. | |
| 0173928 | 3/1986 | European Pat. Off. | 424/482 |
| 2313915 | 1/1977 | France | |
| 2039737 | 8/1980 | United Kingdom | 424/19 |

OTHER PUBLICATIONS

Chemical Abstracts, vol. 100, No. 18, Apr. 30, 1984, p. 367, Abstract 145016c.

Primary Examiner—Thurman K. Page
Attorney, Agent, or Firm—Marla J. Church; Robert Hardy Falk

[57] ABSTRACT

A diltiazem pellet formulation for oral administration comprises a core of diltiazem or a pharmaceutically acceptable salt thereof in association with an organic acid and a lubricant, and a membrane surrounding the core comprising a multiplicity of sequentially applied and dried layers, each layer containing a major proportion of a pharmaceutically acceptable film-forming, water insoluble, naturally occurring polymer and a minor proportion of a pharmaceutically acceptable film-forming, water soluble polymer. The number of layers in the membrane and the ratio of the water soluble to water insoluble polymer being effective to permit release of the diltiazem from the pellet at a rate allowing controlled absorption thereof over a twelve hour period following oral administration.

20 Claims, 4 Drawing Sheets

CONTROLLED ABSORPTION DILTIAZEM FORMULATION

RELATED APPLICATIONS

This application is a continuation-in-part of Ser. No. 684,661 to Donald E. Panoz and Edward J. Geoghegan entitled "CONTROLLED ABSORPTION DILTIAZEM PHARMACEUTICAL FORMULATION" filed Dec. 20, 1984, having a priority of Dec. 22, 1983, based on Irish Patent Application No. 3057/83; Ser. No. 684,661 issued on Jan. 26, 1988 as U.S. Pat. No. 4,721,619.

BACKGROUND OF THE INVENTION

This invention relates to a controlled absorption pharmaceutical formulation and, in particular, to a controlled absorption form of diltiazem for oral administration.

DESCRIPTION OF THE PRIOR ART

Diltiazem-cis-(+)-3-(acetyloxy)-5-[2-(dimethylamino) ethyl]-2,3-dihydro-2-(4-methoxyphenyl)-1,5-benzothiazepin-4(5H)-one, is a benzothiazine derivative possessing calcium antagonist activity. Diltiazem blocks the influx of calcium ions in smooth and cardiac muscle and thus exerts potent cardio-vascular effects. Diltiazem has been shown to be useful in alleviating symptoms of chronic heart disease, particularly angina pectoris and myocardial ischemia and hypertension, while displaying a low incidence of side effects. Diltiazem is conventionally administered in tablet form as (30 mg or 60 mg) diltiazem hydrochloride sold under the Trade Mark Cardizem (Marion Laboratories Inc.). Diltiazem in tablet form (30 mg) is also sold under the Trade Mark Harbesser (Tanabe Seiyaku). Diltiazem is also sold in capsule form.

Conventional diltiazem therapy starts with 30 mg administered 4 times daily. The dosage is gradually increased to 240 mg, given in divided doses three or four times daily, at one- to two-day intervals until an optimum response is obtained. Diltiazem is extensively metabolized by the liver and excreted by the kidneys and in bile. According to professional use information issued by Marion Laboratories Inc., Cardizem is absorbed from the known tablet formulation to about 80% and is subject to an extensive first-pass effect, giving an absolute bioavailability, compared to intravenous administration, of about 40%. Single oral doses of 30 to 120 mg of Cardizem result in peak plasma levels 2-3 hours after administration. Detectable plasma levels occur within 30-60 minutes after administration, indicating that Cardizem is readily absorbed.

The plasma elimination half-life of diltiazem following single or multiple administration is approximately 3-5 hours. Therapeutic blood levels of Cardizem are thought to be in the range of 50-200 ng/ml.

As stated above, conventional diltiazem capsules and tablets are administered three or four times daily. Such frequent drug administration may reduce patient compliance and produces irregular blood levels; thus adverse therapeutic effects can arise.

An article by McAuley, Bruce J. and Schroeder, John S. in Pharmacotherapy 2: 121, 1982 states that peak plasma levels of diltiazem occur within one hour with normal capsules and within 3 to 4 hours with sustained release tablets.

Co-pending U.S. patent application Ser. No. 684,661 filed Dec. 20, 1984, and incorporated herein by reference, describes and claims an effective diltiazem formulation for twice-daily administration. The formulation is distinguished by a characteristic dissolution rate when tested under specified conditions, not least its controlled absorption characteristics in vivo, which offer distinct advantages over existing formulations. However, it has been found with certain formulations prepared in accordance with U.S. patent application Ser. No. 684,661 when manufactured in production batches commensurate with commercial scale manufacture, to the indicated specifications, that the in vitro performance of the formulations, disimproved beyond acceptable limits when stored over the normally required shelf-life periods. This was found to be particularly the case with formulations containing the naturally occurring polymer shellac.

It is an object of the present invention to provide a controlled absorption diltiazem formulation suitable for twice daily administration, which is bioequivalent to our earlier oral formulation of diltiazem and which has good stability over normal shelf-life periods of eighteen months to two years.

DESCRIPTION OF THE INVENTION

Accordingly, the invention provides a diltiazem pellet formulation for oral administration, said pellet comprising a core of diltiazem or a pharmaceutically acceptable salt thereof in association with an organic acid and a lubricant, the diltiazem component and the organic acid being present in a ratio of from 50:1 to 1:1, and a membrane surrounding said core comprising a multiplicity of sequentially applied and dried layers, each layer containing a major proportion of a pharmaceutically acceptable film-forming, water insoluble, naturally occurring polymer and a minor proportion of a pharmaceutically acceptable film-forming, water soluble polymer, the number of layers in said membrane and the ratio of said water soluble to water insoluble polymer being effective to permit release of said diltiazem from said pellet at a rate allowing controlled absorption thereof over a twelve hour period following oral administration.

Preferably, the membrane comprises from 10 to 100 layers and the in vitro dissolution rate of said pellet, when measured in a dissolution apparatus (paddle) according to U.S. Pharmacopoeia XXI in 0.05 M KCl at pH 7.0 substantially corresponds to the following dissolution pattern:

(a) from 0 to 25% of the total diltiazem is released after 4 hours of measurement in said apparatus;
(b) from 20 to 45% of the total diltiazem is released after 6 hours of measurement in said apparatus;
(c) not less than 85% of the total diltiazem is released after 13 hours of measurement in said apparatus.

Diltiazem is widely used in the treatment of chronic heart disease, in particular, in anti-anginal therapy, and the patient for one reason or another (for example, takes the dose later than due, is switching from conventional frequently administered, immediately released products, etc.), may require a rapid attainment of effective therapeutic blood levels of diltiazem for fast relief of onset of anginal attack.

Accordingly, the invention also provides a controlled absorption diltiazem formulation for oral administration, comprising pellets as hereinbefore defined formulated with an amount of fast releasing diltiazem sufficient to achieve a dissolution rate which when measured in a dissolution apparatus (paddle) according to U.S. Pharmacopoeia XXI in 0.05 M KCl at pH 7.0 substantially corresponds to the following dissolution pattern:

(a) from 10 to 35% of the total diltiazem is released after 4 hours of measurement in said apparatus;
(b) 30 to 55% of the total diltiazem is released after a total of 6 hours of measurement in said apparatus; and
(c) not less than 85% of the total diltiazem is released after 13 hours of measurement in said apparatus.

Preferably, the fast releasing diltiazem is present as pellets in an amount of up to 20% by weight.

Most preferably, the pellets which permit fast release of diltiazem comprise pellets having a composition as hereinbefore defined but having a dissolution rate, which when measured in a dissolution apparatus (paddle) according to U.S. Pharmacopoeia XXI in 0.05 M KCl at pH 7.0 substantially corresponds to the following dissolution pattern:

(a) from 35 to 55% of the total diltiazem is released after 2 hours of measurement in said apparatus; and
(b) not less than 90% of the total diltiazem is released after 5 hours of measurement in said apparatus.

Preferably, the diltiazem is in the form of a pharmaceutically acceptable salt thereof, more particularly the hydrochloride salt thereof.

The organic acid is preferably represented by one or more of the following acids: fumaric acid, malic acid or succinic acid. Especially preferred acids are fumaric acid and succinic acid. The diltiazem component and organic acid are preferably present in a ratio of from 10:1 to 2:1, more especially 6:1 to 3:1.

The lubricant is preferably represented by one or more of the following: sodium stearate, magnesium stearate, stearic acid or talc. The diltiazem and lubricant are preferably present in a ratio of from 1:1 to 50:1.

Preferably, the core comprises diltiazem or a pharmaceutically acceptable salt thereof and the associated organic acid and lubricant embedded in a polymeric material. The polymeric material may be rapidly soluble in water or, alternatively, may be freely permeable to diltiazem and water.

The term water soluble polymer as used herein includes polymers which are freely permeable to water such as Eudragit RL. Likewise, the term water insoluble polymer as used herein includes polymers which are slightly permeable to water such as Eudragit RS.

The polymeric material preferably consists solely of a water soluble polymer or a polymer which is freely permeable to diltiazem and water. Alternatively, the polymeric material of the core may include a minor proportion of a water insoluble polymer or a polymer which is slightly permeable to diltiazem and water. The ratio of water soluble/freely permeable to water insoluble/slightly permeable polymer is determined by the particular combination of polymers selected. However, in the case of a core including a water soluble polymer and a water insoluble polymer, the ratio of water soluble polymer to water insoluble polymer will normally be in the range of 1:1 to 50:1, more especially 3:1 to 9:1.

The water soluble polymer is suitably polyvinyl alcohol, polyvinylpyrrolidone, hydroxypropyl cellulose or hydroxypropylmethyl cellulose, polyethylene glycol or a mixture thereof. An especially preferred water soluble polymer is polyvinylpyrrolidone.

A suitable polymer which is freely permeable to diltiazem and water is a polymer sold under the Trade Mark EUDRAGIT RL.

The water insoluble polymer of the core is preferably a water insoluble, naturally occurring polymer or resin. Especially suitable water insoluble, naturally occurring polymers include shellac, chitosan, gumjuniper or a mixture thereof. Shellac is particularly preferred. The water insoluble polymer of the core may also comprise ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) or polyurethane or a mixture thereof.

A suitable polymer which is slightly permeable to diltiazem and water is a polymer sold under the Trade Mark EUDRAGIT RS or a polymer whose permeability is pH dependent and sold under the Trade Mark EUDRAGIT L, EUDRAGIT S or EUDRAGIT E.

EUDRAGIT polymers are polymeric lacquer substances based on acrylates and/or methacrylates.

Polymeric materials sold under the Trade Marks EUDRAGIT RL and EUDRAGIT RS are acrylic resins comprising copolymers of acrylic and methacrylic acid esters with a low content of quaternary ammonium groups and are described in the "EUDRAGIT" brochure of Messrs. Rohm Pharma GmbH (1985) wherein detailed physical-chemical data of these products are given. The ammonium groups are present as salts and give rise to the permeability of the lacquer films. EUDRAGIT RL and RS are freely permeable (RL) or slightly permeable (RS), respectively, independent of pH.

EUDRAGIT L is an anionic polymer synthesized from methacrylic acid and methacrylic acid methyl ester. It is insoluble in acids and pure water. It becomes soluble in a neutral to weakly alkaline milieu by forming salts with alkalis. The permeability of EUDRAGIT L is pH dependent. Above pH 5.0, the polymer becomes increasingly permeable. EUDRAGIT L is described in the "EUDRAGIT L" brochure of Messrs. Rohm Pharma GmbH (1986) wherein detailed physical-chemical data of the product are given. EUDRAGIT E and S are also described in the "EUDRAGIT E" and "EUDRAGIT S" brochures, respectively, of Messrs. Rohm Pharma GmbH (1986).

The core suitably has between 50 and 200 layers, more particularly 125 layers, of the core-forming materials and is built up in a manner known per se.

Preferably, the multi-layer arrangement of diltiazem, organic acid, lubricant and polymeric material is built up on a central inert core, suitably consisting of a nonpareil seed of sugar/starch having an average diameter in the range 0.3–0.8 mm, especially 0.5–0.6 mm, in a conventional coating pan.

The diltiazem, organic acid and lubricant are blended to form a homogenous powder. The blend is suitably passed through an appropriate mesh screen using a milling machine. Alternate layers of a coating solution/-suspension of the polymeric material and the powder are applied to the central inert core so as to build up the multi-layer arrangement of the active core.

The coating solution/suspension of the polymeric material comprises one or more polymers dissolved/-suspended in a suitable solvent or mixture of solvents. The concentration of the polymeric material in the coating solution/suspension is determined by the viscosity of the final solution. Preferably, between 10 and 40 parts of inert cores are used relative to the homogenous powder.

As indicated above the membrane of the film-forming polymer or mixture of polymers surrounding the core has a major proportion of a water insoluble, naturally occurring polymer and a minor proportion of a water soluble polymer, the ratio of water insoluble to water soluble polymer being determined by the inherent solubility characteristics of the polymers selected.

The water soluble polymer may be replaced by a minor proportion of a polymer which is freely permeable to diltiazem and water, the ratio of water insoluble to freely permeable polymer being determined by the inherent permeability/solubility of the respective polymers. The term "water soluble" polymer embraces such freely permeable polymers as indicated above.

The water insoluble, naturally occurring polymer of the membrane is preferably shellac, chitosan, gumjuniper or a mixture thereof. Shellac is especially preferred.

The water soluble polymer of the membrane is any one of those hereinabove specified for the core and includes polymers which are freely permeable to diltiazem and water as hereinabove indicated.

The membrane is built up by applying a plurality of coats of membrane polymer solution or suspension to the core as hereinafter described. The membrane solution or suspension contains the polymer(s) dissolved or suspended, respectively, in a suitable aqueous or organic solvent or mixture of solvents, optionally in the presence of a lubricant. Suitable lubricants are talc, stearic acid, magnesium stearate and sodium stearate. A particularly preferred lubricant is talc. The membrane polymer or mixture of polymers may optionally include a plasticizing agent. The addition of a plasticizing agent to the membrane solution/suspension may be necessary depending on the formulation, to improve elasticity and may also aid in stabilising the polymer film and prevent changes in polymer permeability over prolonged storage. Suitable plasticizing agents include polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil and varying percentages of acetylated monoglycerides.

Preferably, the number of coats of membrane solution or suspension applied is between 10 and 100. The dissolution rate achieved is proportionally slower as the number of membrane coats increases.

The membrane solution or suspension is applied to the active cores in a conventional coating pan as indicated.

Preferably 2-25 ml, and especially 7 to 15 ml, of membrane solution/suspension is applied per coat per kilogram of active cores.

The membrane solution/suspension is applied at a rate of 1-10 coats/day, especially 3 to 6 coats/day, until all of the coats have been applied. Between daily applications the pellets are dried for 16-24 hours, especially 18-21 hours, at a pellet bed temperature of 40°-50° C. This multiple application of layers to form the membrane, and their thorough drying prior to application of the next layer is a critical and surprising feature of the present invention, resulting in a significant improvement in the long term stability of the product whilst still allowing the use of widely available and pharmaceutically acceptable natural polymers.

The pellets may be filled into hard or soft gelatine capsules. The pellets may also be compressed into tablets using a binder and/or hardening agent commonly employed in tabletting such as microcyrstalline cellulose sold under the Trade Mark "AVICEL" or a co-crystallised powder of highly modified dextrins (3% by weight) and sucrose sold under the Trade Mark "DI-PAC" in such a way that the specific dissolution rate of the pellets is maintained.

Figure 1:
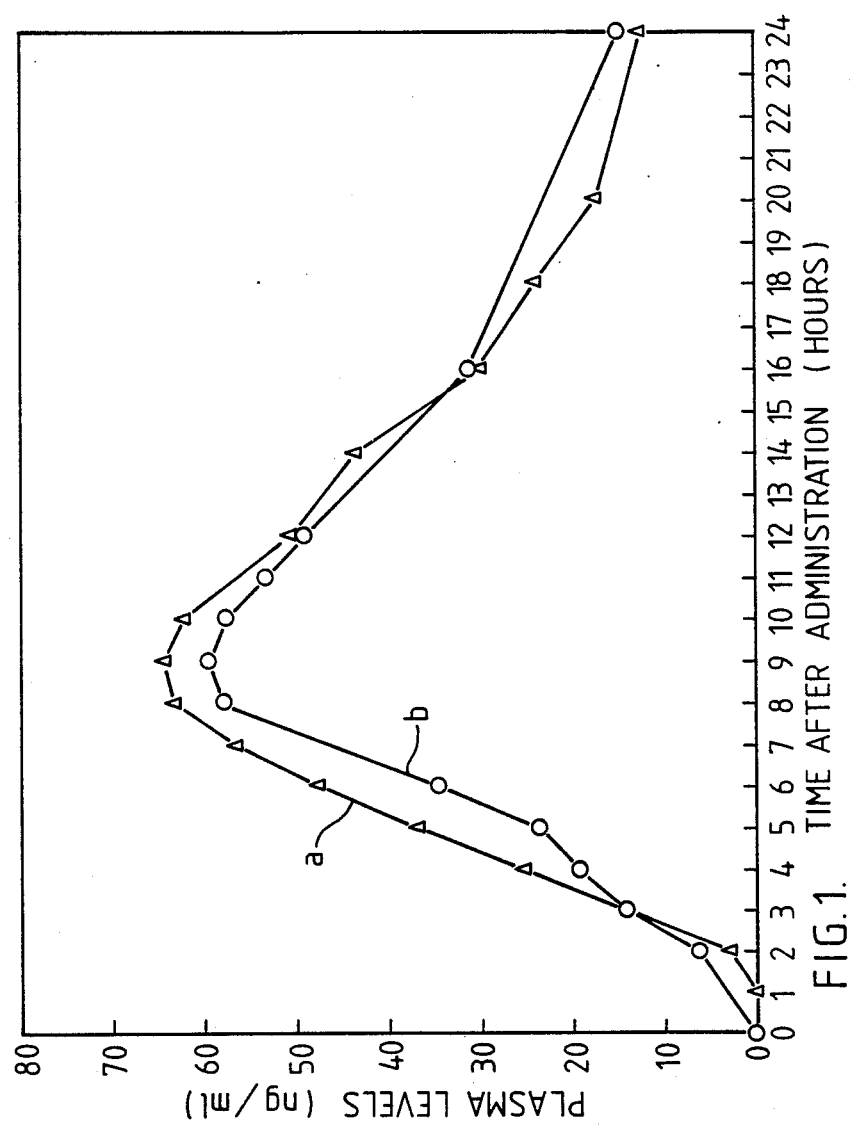
FIG. 1 is a graph of plasma level (ng/ml) of diltiazem versus time after administration (hours) for diltiazem capsules as prepared in Example 6 (curve a) compared with diltiazem capsules prepared in accordance with U.S. patent application Ser. No. 684,661 (curve b)

The invention will be further illustrated by the following Examples:

EXAMPLE 1

Diltiazem hydrochloride (0.75 kg), fumaric acid (0.25 kg) and talc (0.10 kg) were milled and blended to obtain a homogenous powder.

The powder was applied to a starch/sugar seeds (0.6–0.7 mm diameter) (0.5 kg) in a standard coating pan using a coating solution of:

| | |
|---|---|
| 10% Polyvinylpyrrolidone in isopropanol | 80 parts |
| 16.5% Shellac in isopropanol | 20 parts |

The seeds were coated with a measured volume of coating solution followed by dusting on of a measured weight of the powder mix. The coated seeds were allowed to dry and the coating step repeated until all of the powder had been applied. The coated seeds were then dried overnight to remove solvent.

The coated seeds defining the active core of the pellet being prepared were then coated with successive applications of a suspension consisting of:

| | |
|---|---|
| Shellac in isopropanol | 90 parts by volume |
| Polyvinylpyrrolidone in isopropanol | 10 parts by volume |
| Talc | 100 parts by weight | so as to build up a multi-layer membrane surrounding the core. Each coat of membrane suspension comprised 10 ml of suspension per kg of coated seeds. After each coat had been applied the pellets were air dried in the coating pan. The membrane was applied at a rate of 5 coats/day, until the desired number of coats of membrane suspension had been applied. After each daily application of coats, the coated cores were dried at a pellet bed temperature of 50° C. for 18 hours.

The finished pellets were then subjected to a dissolution test. Prior to performing the dissolution test, the pellets were dried to remove all traces of solvent. The dissolution rate of the pellets was tested by the method of U.S. Pharmacopoeia XXI (Paddle Method) in 0.05 M KCl solution adjusted to pH 7.0 and was found to be as follows:

| Time (hours) | Diltiazem hydrochloride % released |
| --- | --- |
| 4 | 3.8 |
| 6 | 24.5 |
| 13 | 102.3 |

EXAMPLE 2

Diltiazem hydrochloride (40 kg), fumaric acid (5 kg) and talc (4 kg) were milled and blended to obtain a homogenous powder.

The powder was applied to starch/sugar seeds (0.5–0.6 mm diameter) (20 kg) in a standard coating pan using a coating solution of:

| 10% Polyvinylpyrrolidone in isopropanol | 80 parts |
| --- | --- |
| 16.5% Shellac in isopropanol | 20 parts |

The seeds were coated with a measured volume of coating suspension followed by dusting on of a measured weight of the powder mix. The coated seeds were allowed to dry and the coating step repeated until all of the powder had been applied. The coated seeds were then dried overnight to remove solvent.

The coated seeds defining the active core of the pellet being prepared were then coated with successive applications of a suspension consisting of:

| Shellac in isopropanol | 90 parts by volume |
| --- | --- |
| Polyvinylpyrrolidone in isopropanol | 10 parts by volume |
| Talc | 100 parts by weight | so as to build up a multi-layer membrane surrounding the core.

Each coat of membrane suspension comprised 12 ml of suspension per kg of coated seeds. After each coat had been applied the pellets were air dried in the coating pan. The membrane was applied at a rate of 4 coats/day until the desired number of coats of membrane suspension had been applied. After each daily application of coats the coated cores were dried at a pellet bed temperature of 46° C. for 20 hours.

The finished pellets were then subjected to a dissolution test. Prior to performing the dissolution test, the pellets were dried to remove all traces of solvent.

The dissolution rate of the pellets was tested by the method of U.S. Pharmacopoeia XXI (Paddle Method) in 0.05 M KCl solution adjusted to pH 7.0 and was found to be as follows:

| Time (hours) | Diltiazem hydrochloride % released |
| --- | --- |
| 4 | 13.1 |
| 6 | 34.5 |
| 13 | 98.6 |

EXAMPLE 3

Example 2 was repeated and the pellets obtained with the indicated dissolution pattern corresponded to slow release pellets. Fast release pellets were prepared following the procedure of Example 2 except that a lesser number coats of membrane suspension were applied so as to obtain a dissolution of:

| Time (hours) | Diltiazem hydrochloride % released |
| --- | --- |
| 2 | 47.0 |
| 5 | 94.3 |

The slow and fast release pellets were then combined, such that the fast release pellets amounted to 15% by weight of the total blend, to produce a blend which was then subjected to a dissolution test.

Prior to performing the dissolution test, both the slow and fast release pellets were dried to remove all traces of solvent. The dissolution rate of the pellets (blend) was tested by the method of U.S. Pharmacopoeia XXI (Paddle Method) in 0.05 M KCl solution adjusted to pH 7.0 and was found to be as follows:

| Time (hours) | Diltiazem hydrochloride % released |
| --- | --- |
| 4 | 21.1 |
| 6 | 38.4 |
| 13 | 96.2 |

EXAMPLE 4

Example 2 was repeated except the starch/sugar seed size used was 0.4–0.5 mm and the coating solution used was:

| 5.0% Hydroxypropylmethyl cellulose in methylene chloride/methanol 50:50 | 80 parts |
| --- | --- |
| 5.0% Gumjuniper in ethanol | 20 parts |

The membrane suspension used was:

| 7.5% Polyvinylpyrrolidone in isopropanol | 10 parts by volume |
| --- | --- |
| 15.0% Gumjuniper in ethanol | 90 parts by volume |
| Isopropanol | 100 parts by volume |
| Talc | 100 parts by weight |

Slow and fast release pellets were prepared as in Example 3. A blend of these pellets was prepared containing 15% by weight of the fast release pellets to achieve a dissolution profile as follows:

| Time (hours) | Diltiazem hydrochloride % released |
| --- | --- |
| 4 | 23.2 |

-continued

| Time (hours) | Diltiazem hydrochloride % released |
|---|---|
| 6 | 39.3 |
| 13 | 99.6 |

EXAMPLE 5

Example 2 was repeated except the coating solution used was as follows:

| | |
|---|---|
| 7.5% Polyvinylpyrrolidone in ethanol | 90 parts |
| 5.0% Chitosan in ethanol | 10 parts |

The membrane suspension used was:

| | |
|---|---|
| 2.5% Polyethylene glycol in ethanol | 5 parts |
| 5.0% Polyvinylpyrrolidone in ethanol | 15 parts |
| 5% Chitosan in ethanol | 80 parts |

Slow and fast release pellets were prepared as in Example 3. A blend of these pellets was prepared containing 15% by weight of the fast release pellets so as to achieve a dissolution profile as follows:

| Time (hours) | Diltiazem hydrochloride % released |
|---|---|
| 4 | 28.3 |
| 6 | 45.6 |
| 13 | 98.3 |

EXAMPLE 6

Pellets according to Example 2 were filled directly into hard gelatine capsules without the addition of any extra ingredients so as to obtain capsules containing 120 mg of diltiazem hydrochloride.

EXAMPLE 7

A blend of pellets according to Example 3 was filled directly into hard gelatine capsules without the addition of any extra ingredients so as to obtain capsules containing 120 mg diltiazem hydrochloride.

PHARMACOLOGICAL DATA FOR THE DILTIAZEM FORMULATION OF EXAMPLE 6

A single-dose study of the formulation of Example 6 was performed in 6 young healthy male subjects.

The formulation was administered as a single 120 mg capsule at 0 hours and plasma concentration of diltiazem was determined at intervals over 24 hours. The results are given in Table 1.

TABLE 1

| MEAN DILTIAZEM PLASMA CONCENTRATIONS (ng/ml) | |
|---|---|
| Time (hours) | Formulation of Example 6 |
| 0.0 | 0.0 |
| 1.00 | 0.0 |
| 2.00 | 2.75 |
| 4.00 | 25.35 |
| 5.00 | 36.83 |
| 6.00 | 47.67 |
| 7.00 | 56.50 |
| 8.00 | 63.17 |
| 9.00 | 64.33 |
| 10.00 | 62.17 |
| 12.00 | 50.50 |

TABLE 1-continued

| MEAN DILTIAZEM PLASMA CONCENTRATIONS (ng/ml) | |
|---|---|
| Time (hours) | Formulation of Example 6 |
| 14.00 | 43.50 |
| 16.00 | 30.33 |
| 18.00 | 24.17 |
| 20.00 | 17.50 |
| 24.00 | 12.42 |

FIG. 1 is a graph of plasma levels (ng/ml) of diltiazem versus time after administration (hours) for a single dose (120 mg) of diltiazem capsules prepared in Example 6 (curve a) compared with a single dose (120 mg) of diltiazem capsules prepared in Example 4 (curve b) of U.S. patent application Ser. No. 684,661. As will be appreciated, the data for the formulation of Example 4 of U.S. Patent Application Ser. No. 684,661 was obtained from a different group of subjects to that of present Example 6, thus making any comparison of bioavailability purely indicative. It will be observed from FIG. 1 that a virtually identical absorption pattern is obtained for each formulation, consistent with twice-daily administration. Hence it is submitted the actual bioavailability values would have been similar if the two formulations had been tested in the same subjects.

PHARMACOLOGICAL DATA FOR THE DILTIAZEM FORMULATION OF EXAMPLE 7

A steady-state, two-way cross-over study comparing the formulation of Example 7 against conventional immediate release tablets (reference) in 12 young healthy male subjects was carried out.

The formulation of Example 7 was administered as a single 120 mg capsule at 0 and 12 hours (i.e. b.i.d.), while the reference product was administered as a single 60 mg tablet at 0, 6, 12 and 18 hours (i.e. q.i.d.). Plasma concentration of diltiazem was determined at intervals over 24 hours and the results are given in Table 2. Pharmacokinetic data is given in Table 3.

TABLE 2

| MEAN DILTIAZEM CONCENTRATIONS (ng/ml) - (Day 5 data) | | |
|---|---|---|
| Hour | Reference | Formulation of Example 7 |
| 0.0 | 81.83 | 94.00 |
| 0.5 | 85.50 | — |
| 1.0 | 121.25 | 88.42 |
| 2.0 | 153.42 | 88.58 |
| 3.0 | 166.00 | — |
| 4.0 | 140.17 | 116.75 |
| 6.0 | 90.67 | 148.06 |
| 6.5 | 78.33 | — |
| 7.0 | 96.92 | 153.92 |
| 8.0 | 121.83 | 139.92 |
| 9.0 | 126.33 | 116.75 |
| 10.0 | 103.08 | 99.08 |
| 12.0 | 71.08 | 77.17 |
| 12.5 | 62.17 | — |
| 13.0 | 72.75 | — |
| 14.0 | 88.17 | 61.25 |
| 15.0 | 104.92 | — |
| 16.0 | 99.83 | 68.83 |
| 18.0 | 73.17 | 102.08 |
| 18.5 | 65.25 | — |
| 19.0 | 81.67 | — |
| 20.0 | 103.92 | 125.92 |
| 21.0 | 112.00 | — |
| 22.0 | 108.33 | — |
| 24.0 | 82.00 | 93.25 |

TABLE 3

PHARMACOKINETIC EVALUATION OF DAY 5 DATA (n = 12)

| Parameters | Reference | Formulation of Example 7 |
|---|---|---|
| AUC (0-24h) | 2474.88 | 2466.00 |
| F (t)% | 100.00 | 99.18 |
| Cmax | 172.08 | 163.33 |
| tmax | 2.75 | 6.92 |

Figure 2:
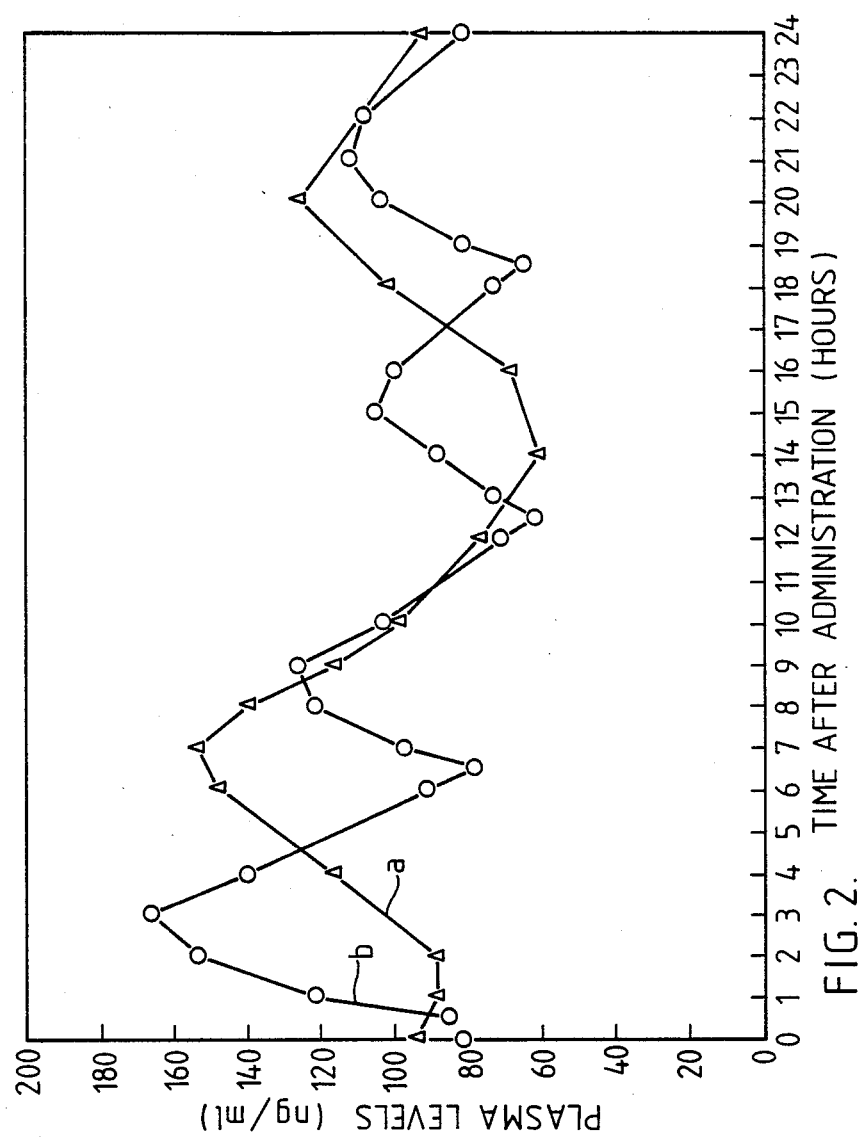
FIG. 2 is a graph of plasma level (ng/ml) of diltiazem versus time after administration (hours) for diltiazem capsules as prepared in Example 7 (curve a) compared with conventional tablets (curve b)

FIG. 2 is a graph of plasma levels (ng/ml) of diltiazem versus time after administration (hours) for a single dose (120 mg) of diltiazem capsules prepared in Example 7 (curve a) compared with a single dose (60 mg) of reference tablets administered as indicated above.

It will be observed from the data presented in Table 3 that the formulation of Example 7 is 99.18% bioavailable compared to reference (=100%), and has a practically identical Cmax and AUC (0-24h). However, the formulation of Example 7 has greatly extended tmax (6.92 hours compared to 2.75 hours for reference) which satisfies the criteria for controlled absorption orally administered drugs, and further shows a reduction in peak-to-trough fluctuations as indicated in FIG. 2.

Experiments were carried out to compare the stability of the pellet formulation according to the invention with formulation of U.S. patent application Ser. No. 684,661.

Figure 3:
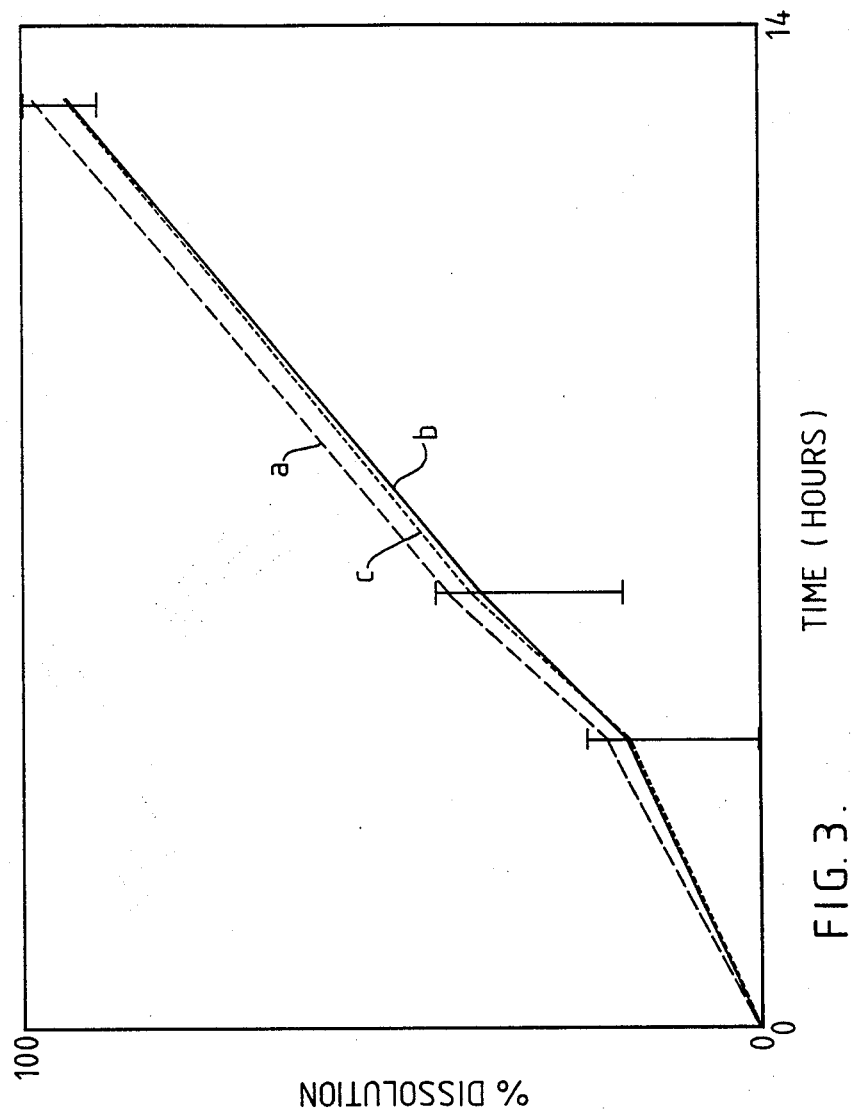
FIG. 3 is a graph of dissolution (%) versus time (hours) of a batch of pellets prepared in accordance with Example 2 and tested at different times after manufacture.
Figure 4:
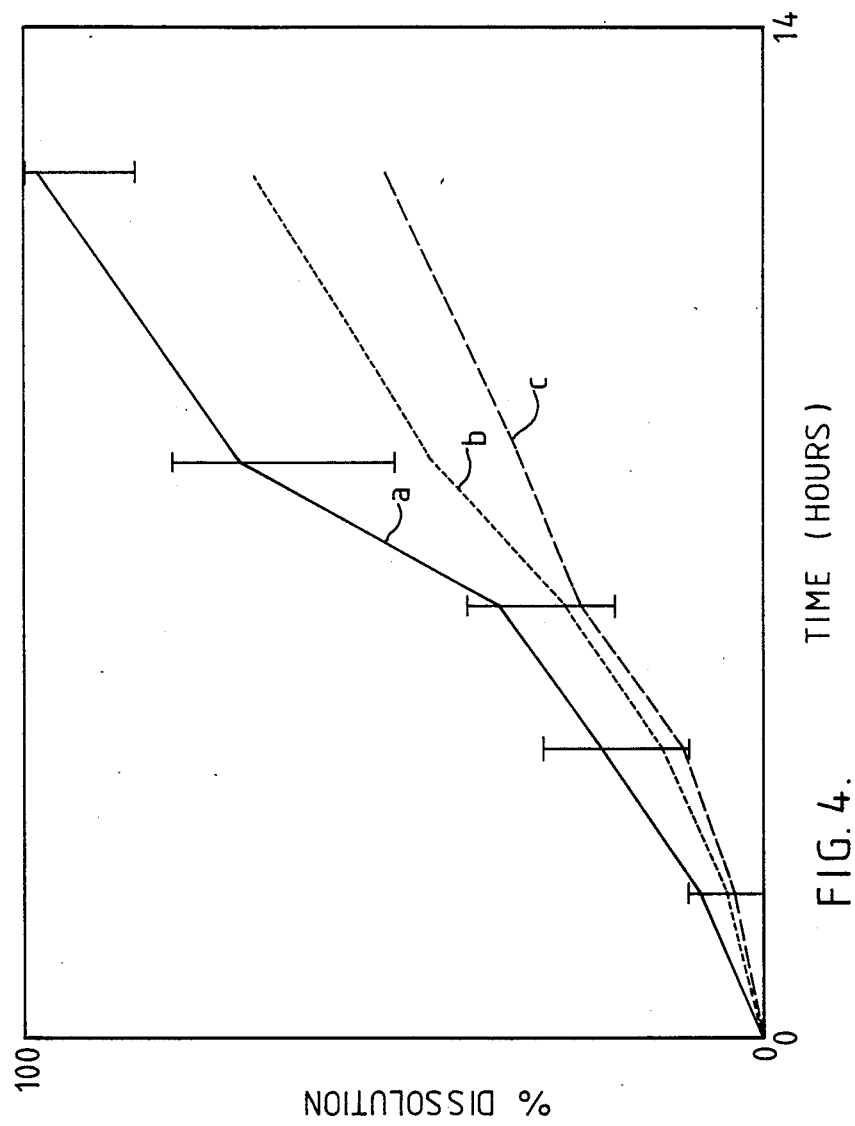
FIG. 4 is a similar graph of dissolution (%) (hours) of a batch of pellets prepared in accordance with Example 2 of U.S. patent application Ser. No. 684,661.

Dissolution tests of the type described in Example 1 were carried out on three batches of the pellet formulation of Example 2 after storage in ambient conditions over a period concomitant with commercial shelf-life, in accordance with established criteria. The results are presented in FIG. 3 which is a graph of dissolution (%) versus time (hours) for the formulation of Example 2. In FIG. 3 curve a represents the batch tested after 3 months of storage, curve b the batch tested after 6 months of storage and curve c the batch tested after 18 months of storage. Identical dissolution tests under identical conditions were carried out on three batches of a pellet formulation prepared in accordance with Example 2 of U.S. patent application Ser. No. 684,661. The results are presented in FIG. 4 which again is a graph of dissolution (%) versus time (hours) for the formulation in question. In FIG. 4 curve a represents the batch tested after 3 months of storage, curve b the batch tested after 6 months of storage and curve c the batch tested after 18 months of storage, A comparison of FIGS. 3 and 4 demonstrates the stability of the formulation of the present invention relative to the formulation of U.S. patent application Ser. No. 684,661, as indicated by the error bars. As will be observed the formulation of U.S. patent application Ser. No. 684,661 under the specified conditions is unstable and therefore is commercially used, would require excessive inventory control procedures.

The formulation according to the invention, which is characterised by a specific in vitro dissolution rate and a more controlled manufacturing process, has excellent stability over the normal marketing shelf-life (18 months to 2 years) in terms of both in vivo and in vitro performance.

What we claim is:

1. A diltiazem pellet formulation for oral administration, said pellet comprising a core of diltiazem or a pharmaceutically acceptable salt thereof in association with an organic acid and a lubricant, the diltiazem component and the organic acid being present in a ratio of from 50:1 to 1:1, and a membrane surrounding said core comprising a multiplicity of sequentially applied and dried layers, each layer containing a major proportion of a pharmaceutically acceptable film-forming, water insoluble, naturally occurring polymer and a minor proportion of a pharmaceutically acceptable film-forming, water soluble polymer, the number of layers in said membrane and the ratio of said water soluble to water insoluble polymer being effective to permit release of said diltiazem from said pellet at a rate allowing controlled absorption thereof over a twelve hour period following oral administration.

2. A formulation as claimed in claim 1, wherein said membrane comprises from 10 to 100 layers and the in vitro dissolution rate of said pellet, when measured in a dissolution apparatus (paddle) according to U.S. Pharmacopoeia XXI in 0.05 M KCl at pH 7.0, substantially corresponds to the following dissolution pattern:
   (a) from 0 to 25% of the total diltiazem is released after 4 hours of measurement in said apparatus;
   (b) from 20 to 45% of the total diltiazem is released after 6 hours of measurement in said apparatus; and
   (c) not less than 85% of the total diltiazem is released after 13 hours of measurement in said apparatus.

3. A pellet formulation according to claim 2, wherein the diltiazem or pharmaceutically acceptable salt thereof and organic acid are present in a ratio of from 10:1 to 2:1.

4. A pellet formulation according to claim 1 wherein the core comprises:
   (a) a powder mixture containing diltiazem or a pharmaceutically acceptable salt thereof, an organic acid selected from the group consisting of fumaric acid, malic acid and succinic acid, and a lubricant, and
   (b) a polymeric material containing a major proportion of a pharmaceutically acceptable water soluble polymer and a minor proportion of a pharmaceutically acceptable water insoluble polymer,
said core comprising layers of said powder mixture and said polymeric material superimposed one upon the other and said polymeric material being present in an amount effective to ensure that all of said powder mixture is coated into said core.

5. A pellet formulation according to claim 1 wherein the water soluble polymer in the core or membrane is the same or different and is selected from the group consisting of polyvinyl alcohol, polyvinylpyrrolidone, hydroxypropyl cellulose, hydroxypropylmethyl cellulose and polyethylene glycol or a mixture thereof.

6. A pellet formulation according to claim 1, wherein the water soluble polymer in the core or membrane is replaced by a polymeric material which is freely permeable to diltiazem and water and comprises a copolymer of acrylic and methacrylic acid esters.

7. A pellet formulation according to claim 1 wherein the water insoluble polymer in the core or membrane is the same or different water insoluble, naturally occurring polymer or resin.

8. A pellet formulation according to claim 7, wherein the water insoluble polymer is selected from the group consisting of shellac, chitosan and gumjuniper or a mixture thereof.

9. A pellet formulation according to claim 4, wherein the water insoluble polymer in the core is selected from the group consisting of ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly (methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) and polyurethane or a mixture thereof.

10. A pellet formulation according to claim 4, wherein the water insoluble polymer in the core is replaced by a polymeric material which is slightly permeable to diltiazem and water and comprises a copolymer of acrylic and methacrylic acid esters.

11. A pellet formulation according to claim 4, wherein the diltiazem, organic acid, lubricant and polymeric material are built up on an inert core.

12. A pellet formulation according to claim 11, wherein the inert core is a non-pareil seed of sugar/starch having an average diameter in the range 0.3-0.8 mm.

13. A pellet formulation according to claim 1, which includes a plasticizing agent selected from the group consisting of polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil and an acetylated monoglyceride.

14. A pellet formulation according to claim 1, which contains diltiazem hydrochloride as the active ingredient.

15. A process for the production of a pellet formulation according to claim 1, which comprises forming a core of diltiazem or a pharmaceutically acceptable salt thereof, an organic acid and a lubricant and enclosing the core in a membrane of a film-forming polymer or mixture thereof as defined in claim 1 which permits release of the diltiazem or the pharmaceutically acceptable salt thereof, said membrane being applied to the core by applying a plurality of coats of membrane solution or suspension at a rate of 1 to 10 coats/day, followed by drying at a pellet bed temperature in the range 40°-50° C., for a period of 16-24 hours.

16. A controlled absorption diltiazem formulation for oral, administration comprising pellets as claimed in claim 1, formulated with an amount of fast releasing diltiazem sufficient to achieve a dissolution rate which when measured in a dissolution apparatus (paddle) according to U.S. Pharmacopoeia XXI in 0 05 M KCl at pH 7.0 substantially corresponds to the following:
(a) from 10 to 35% of the total diltiazem is released after 4 hours of measurement in said apparatus;
(b) from 30 to 55% of the total diltiazem is released after 6 hours of measurement in said apparatus; and
(c) not less than 85% of the total diltiazem is released after 13 hours of measurement in said apparatus.

17. A controlled absorption diltiazem formulation according to claim 16, which comprises a blend of said pellet's together with up to 20% by weight of pellets which permit fast release of diltiazem.

18. A controlled absorption diltiazem formulation according to claim 17, wherein the fast release diltiazem pellets have a composition corresponding to the said composition of the pellets, but having a dissolution rate, which when measured in a dissolution apparatus (paddle) according to U.S. Pharmacopoeia XXI in 0.05 M KCl at pH 7.0 substantially corresponds to the following dissolution pattern:
(a) from 35 to 55% of the total diltiazem is released after 2 hours fo measurement in said apparatus; and
(b) not less than 90% of the total diltiazem is released after 5 hours of measurement in said apparatus.

19. A capsule or tablet, comprising a formulation of pellets according to claim 1.

20. A capsule or tablet comprising a formulation of pellets according to claim 16.

* * * * *